United States Patent [19]

Akizawa et al.

[11] Patent Number: 5,510,515
[45] Date of Patent: Apr. 23, 1996

[54] PROCESS FOR PURIFYING POLAR VINYL COMPOUND

[75] Inventors: Toshiyuki Akizawa; Hiroyuki Hasegawa; Hitoshi Nakamura, all of Oita; Katsufumi Urabe, Kobe; Shingo Yoshida, Kobe; Yuichi Matsuda, Kobe; Tamiharu Sakai, Kobe, all of Japan

[73] Assignees: Showa Denko K. K., Tokyo; Kabushiki Kaisha Kobe Seiko Sho, Hyogo, both of Japan

[21] Appl. No.: 305,962

[22] Filed: Sep. 16, 1994

[30] Foreign Application Priority Data

| Sep. 21, 1993 | [JP] | Japan | 5-235011 |
| Sep. 22, 1993 | [JP] | Japan | 5-236824 |
| Sep. 22, 1993 | [JP] | Japan | 5-236825 |

[51] Int. Cl.$^6$ .................................................. C07C 67/48
[52] U.S. Cl. .................................................. 560/218
[58] Field of Search ............................................ 560/218

[56] References Cited

U.S. PATENT DOCUMENTS

| 4,337,215 | 6/1982 | Doi et al. | 260/513 N |
| 4,401,516 | 8/1983 | Matzinger | 203/33 |
| 4,780,568 | 10/1988 | Pascoe | 562/599 |

FOREIGN PATENT DOCUMENTS

| 336564 | 3/1989 | European Pat. Off. |
| 475836 | 9/1991 | European Pat. Off. |
| 2904444 | 2/1979 | Germany. |
| WOA9418166 | 8/1994 | WIPO. |

OTHER PUBLICATIONS

*Database WPI*, Week 8828, Derwent Publications, Ltd., London, GB; AN 88–194690 and JP–A–63 132 868 (Sumitomo Chem Ind KK) 4 Jun. 1988 (abstract).
*Database WPI*, Week 9320, Derwent Publications, Ltd., London, GB; AN 93–161786 and JP–A–5 092 102 (Idemitsu Petrochem Co.) 16 Apr. 1993 (abstract).

*Primary Examiner*—Paul J. Killos
*Attorney, Agent, or Firm*—Sughrue, Mion, Zinn, Macpeak & Seas

[57] ABSTRACT

The present invention provides a process for purifying a polar vinyl compound, comprising pressurizing a crude polar vinyl compound containing impurities such as polymerization inhibiting substances and components of starting materials used in preparation of the polar vinyl compound to 500–3000 atm at 0°–100° C., the polar vinyl compound having at least one member selected from among oxygen, nitrogen and sulfur atoms, to thereby form crystals of the polar vinyl compound and separating the crystals of the polar vinyl compound from a liquid phase under pressure.

12 Claims, 2 Drawing Sheets

PROCESS FOR PURIFYING POLAR VINYL COMPOUND

TECHNICAL FIELD

The present invention relates to a process for purifying a polar vinyl compound such as N-vinylcarboxamides. More particularly, it is concerned with a process for obtaining a highly purified polar vinyl compound from a mixture of a polar vinyl compound, impurities such as polymerization inhibiting substances and starting materials used in preparation of the polar vinyl compound, that is, from a polar vinyl compound containing impurities (hereinafter referred to as "crude polar vinyl compound").

BACKGROUND ART

A wide variety of useful polymers are obtained by polymerizing a vinyl compound through an addition polymerization, e.g., a radical, a cationic or an anionic polymerization. This polymerization proceeds through a chain reaction, so that, when the vinyl compound contains chain terminating or chain transferring compounds as formed during the production of the vinyl compound, adverse effects are caused such as retardation of the polymerization reaction and decrease of the molecular weight of the obtained polymer. Many of these polymerization inhibiting substances give adverse effect on the polymerization reaction even if their amount is very small. Therefore, it is needed to completely eliminate the above polymerization inhibiting substances, for imparting excellent polymerizability (polymerization activity) to the vinyl compound.

A polymerization inhibitor is often added to a vinyl compound having a radical polymerization activity during or after the production thereof in order to inhibit the polymerization during the production, storage and transportation. Therefore, although a polymerization initiator is often added in an amount sufficient to countervail the effect of the polymerization inhibitor in the polymerization of the vinyl compound, it is preferred that the polymerization inhibitor be removed from the vinyl compound prior to the polymerization, for obtaining a polymer of high quality.

However, it is often difficult to remove the polymerization inhibitor and other polymerization inhibiting substances from a vinyl compound containing an oxygen, a nitrogen or a sulfur atom, i.e., a vinyl compound having a polar group (polar vinyl compound). When the polar vinyl compound is purified by distillation, it is generally required to withdraw the same in vacuum and simultaneously at a temperature not lower than the melting point thereof because the boiling and melting points of the polar vinyl compound are relatively high, so that the operating conditions of the distillation are often extremely restrained. Further, there is the danger that the polar vinyl compound is polymerized during the distilling operation. Therefore, the practical use in industry of the distillation for the purification of the polar vinyl compound involves problems.

Also, the polar vinyl compound is purified by recrystallization. This requires purification of the recrystallization solvent and drying of the product. Further, there is the danger that a polymer of the polar vinyl compound is formed by local heating in the drying step. Therefore, the industrial purification of the polar vinyl compound by recrystallization involves economic disadvantages.

The method of effecting adsorption and removal of polymerization inhibiting substances by passing a solution of a vinyl compound, especially a polar vinyl compound through a column packed with an ion exchange resin or active carbon does not require separation of the vinyl compound from the treated solution and hence is advantageous in the direct use thereof in polymerization, so that it is widely utilized in the purification of the polar vinyl compound. However, a solvent suitable for use not only in adsorption operation but also in polymerization reaction must be selected taking the availability and economy thereof into account, and it has practically been unfeasible to find a solvent meeting all of these requirements. Further, it is necessary to conduct regeneration or exchange of an adsorbent, and this involves inconvenience in the execution on an industrial scale. Still further, a crystallized vinyl compound is sometimes demanded when the compound is transported to a remote place, when it is stored in a cold place, or depending on the use thereof. In that case, the same problems as mentioned with respect to the above purification method may be involved.

Japanese Patent Publication No. 56(1981)-41282 discloses a process comprising applying a high pressure to a mixture to thereby crystallize a component and separating the crystals from a liquid phase under pressure, generally known as the pressure crystallization process. This pressure crystallization process is known to be applicable to separation of position isomers of xylene, naphthalenes and cresol and to separation of alkylated phenols from phenol alkylation reaction mixtures, as disclosed Japanese Patent Laid-open Publication Nos. 62(1987)-209034, 1(1989)-250329 and 4(1992)-120027. However, there has been no disclosure regarding the application of the pressure crystallization process to the vinyl compound for imparting excellent polymerizability to a polymerizable vinyl compound.

For example, it is known hat the N-vinylcarboxamide can be produced by first synthesizing an N-(1-alkoxyethyl)carboxamide from a carboxamide, acetaldehyde and an alcohol and then performing thermal or catalytic decomposition of the N-(1-alkoxyethyl)carboxamide. However, the properties, especially the boiling point and solubility of the N-vinylcarboxamide are very close to those of the unreacted carboxamide and N-(1-alkoxyethyl)carboxamide, so that their separation is not easy, although some methods have been proposed.

Japanese Patent Laid-open Publication No. 61(1986)-286069 discloses an extractive separation using water and an aromatic hydrocarbon because the mingling of formamide as the unreacted starting material into the N-vinylformamide cannot be avoided in the distillation.

Another known advantageous process for producing the N-vinylcarboxamide comprises first synthesizing an ethylidenebiscarboxamide from acetaldehyde and a carboxamide and decomposing the ethylidenebiscarboxamide into the carboxamide and the N-vinylcarboxamide. This process produces the carboxamide and the N-vinylcarboxamide which have similar properties in equimolar amounts, and their separation is very difficult. Japanese Patent Laid-open Publication Nos. 63(1988)-132868 and 2(1990)-188560 and U.S. Pat. No. 4,401,516 respectively disclose a technique of cooling crystallization from an organic solvent mixture, a technique of extraction with an aqueous solution of an inorganic salt and an aromatic hydrocarbon and a technique of extractive distillation with a polyhydric alcohol.

However, it is difficult to obtain a satisfactorily purified N-vinylcarboxamide irrespective of any of the above techniques applied. Further, the extraction technique requires expensive organic solvents, and thus equipment for recovering and purifying the same. Still further, the N-vinylcarboxamide is relatively unstable in water, so that there is the danger that the N-vinylcarboxamide undergoes hydrolysis during the extracting operation. Thus, the extraction technique is not an industrially satisfactory method. On the other hand, the technique of cooling crystallization from an organic solvent involves the same problems concerned with the use of the organic solvent as in the extracion technique, and in addition disadvantageously requires a drying step and involves the problem that there is the possibility of thermal polymerization of the N-vinylcarboxamide. With respect to the extractive distillation technique, an organic solvent is used, so that the reflux ratio must be increased for attaining desired rectification effect, thereby necessitating heating of the N-vinylcarboxamide for a prolonged period of time.

All of the above conventional techniques disclosed cannot ensure efficient stable separation of a highly purified polar vinyl compound such as N-vinylcarboxamides having high polymerizability on an industrial scale.

OBJECT OF THE INVENTION

The object of the present invention is to provide a process for purifying a polar vinyl compound, in which a vinyl compound having excellent polymerizability can be produced by removing impurities, such as polymerization inhibiting substances and starting materials used in preparation of the polar vinyl compound, from a vinyl compound having a polar group (e.g., N-vinylcarboxamide, etc.).

SUMMARY OF THE INVENTION

According to the present invention, there is provided a process for purifying a polar vinyl compound, comprising pressurizing a crude polar vinyl compound containing impurities such as polymerization inhibiting substances and starting materials used in preparation of the polar vinyl compound to 500–3000 atm at 0°–100° C., the polar vinyl compound having at least one member selected from among oxygen, nitrogen and sulfur atoms, to thereby form crystals of the polar vinyl compound and separating the crystals of the polar vinyl compound from a liquid phase under pressure.

In an advantageous mode for carrying out the invention, it is preferred that the polar vinyl compound be a compound represented by a formula selected from among the following general formulae (1), (2) and (3):

$$CH_2=CHNR^1COR^2 \qquad (1)$$

wherein each of $R^1$ and $R^2$ independently represents a hydrogen atom or a methyl group,

$$CH_2=CR^1COOR^2 \qquad (2)$$

wherein $R^1$ represents a hydrogen atom, a methyl group or a cyano group, and $R^2$ represents a hydrogen atom, an alkali metal, an alkyl group having 1 to 5 carbon atoms or a lower alkyl group (preferably a $C_2$–$C_4$ alkyl group) substituted with a hydroxyl, a dialkylamino or a quaternary ammonium group, and

$$CH_2=CR^1CONR^2R^3 \qquad (3)$$

wherein $R^1$ represents a hydrogen atom or a methyl group, and each of $R^2$ and $R^3$ independently represents a hydrogen atom, an alkyl group having 1 to 5 carbon atoms or a lower alkyl group (preferably a $C_2$–$C_4$ alkyl group) substituted with a hydroxyl, a dialkylamino, a sulfonic acid or a quaternary ammonium group.

In other advantageous modes for carrying out the invention, it is preferred that the crude polar vinyl compound contain the polar vinyl compound in an amount of at least 40% by weight, and that especially it be a crude N-vinylcarboxamide containing the N-vinylcarboxamide in an amount of at least 40% by weigh. Further, it is preferred that the crystallization from the crude polar vinyl compound be performed in the presence of an alcohol or a basic compound.

In addition, according to the present invention, there is provided a process for purifying a polar vinyl compound, including separating a polar vinyl compound from a crude polar vinyl compound (e.g., crude N-vinylcarboxamide) and purifying the same to obtain a highly purified polar vinyl compound, which comprises the steps of:

(1) crystallizing a polar vinyl compound from a crude polar vinyl compound according to the pressure crystallization process, and separating the crystals of the polar vinyl compound from a liquid phase to thereby obtain a highly purified polar vinyl compound;

(2) subjecting the liquid phase separated in the first step to the pressure crystallization process conducted at temperatures lower than in the first step, or the cooling crystallization process, thereby obtaining second crystals of the polar vinyl compound; and (3) recycling the second crystals obtained in the second step into the crude polar vinyl compound for treatment in the first step.

BRIEF DESCRIPTION OF THE DRAWINGS

In FIGS. 1 and 2, A is a reaction distillation column, B is a distillation column, C is a countercurrent extraction column, D is a reactor for conversion of an ether amide, E is an acetal stripper, F is a methanol stripper, G is a reactor for decomposing of an ether amide, H is an N-vinylacetamide vacuum distillation column, I is a pressure crystallizer, and J is a pressure crystallizer or cooling crystallizer. The full lines and numerals 1 to 21 indicate the flow of materials.

DETAILED DESCRIPTION OF THE INVENTION

Purification of Polar Vinyl Compound

Figure 1:
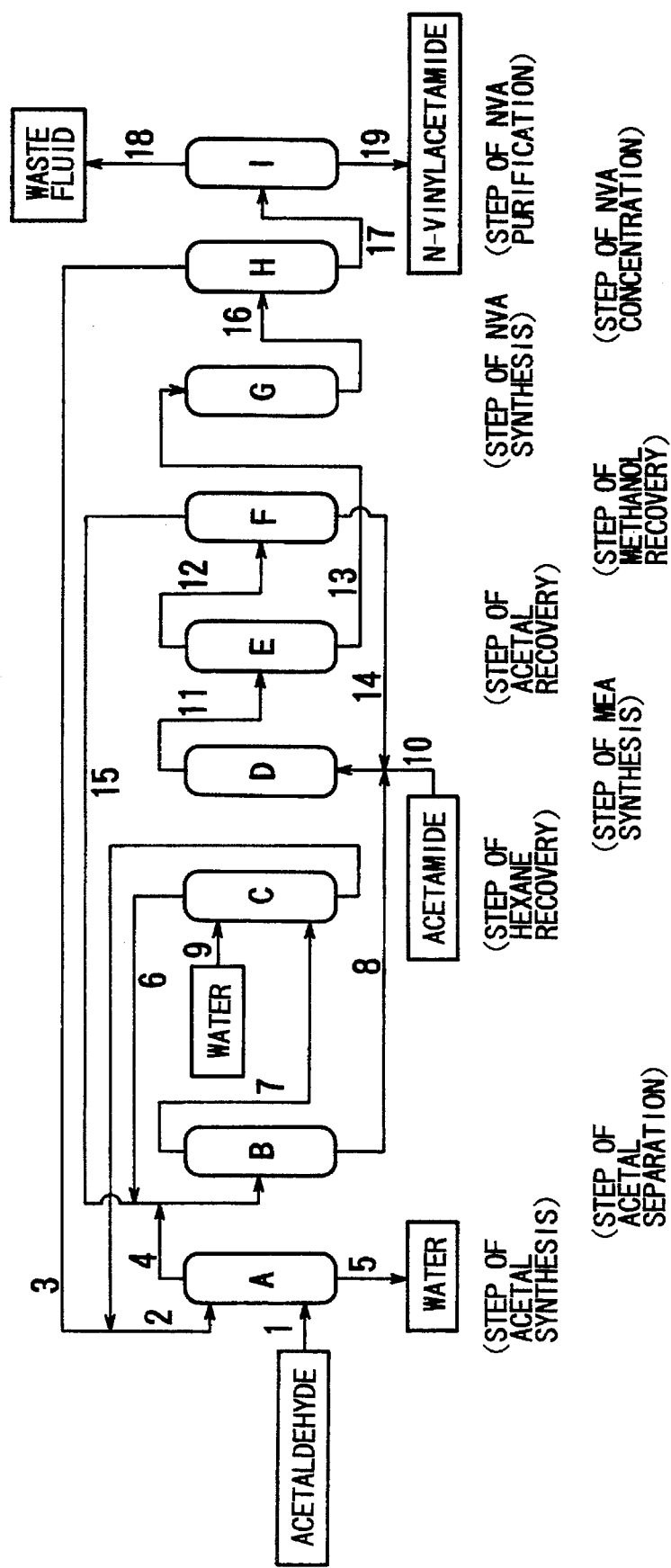
FIGS. 1 and 2 are conceptual diagrams illustrating the steps of production and purification of N-vinylacetamide.

The first process for purifying a polar vinyl compound according to the present invention will now be described in greater detail.

In the first process for purifying a polar vinyl compound according to the present invention, a vinyl compound (hereinafter frequently referred to as "crude polar vinyl compound") having at least one member selected from among oxygen, nitrogen and sulfur atoms, in which impurities such as polymerization inhibiting substances (e.g., polymerization inhibitor) and starting materials (including intermediates) used in preparation of the polar vinyl compound are contained, is treated by the pressure crystallization process, followed by separation of the polar vinyl compound from the above impurities, to thereby purify the polar vinyl compound.

In the present invention, the crystallization pressure is generally in the range of 500 to 3000 atm and preferably in the range of 1000 to 2000 atm. When the crystallization pressure is lower than 500 atm, not only is the improvement in the polymerizability of the resultant polar vinyl compound not substantial but also the amount of crystals obtained per crystallization operation is small to thereby cause the productivity to be low to economic disadvantage. On the other hand, even if the crystallization is performed under a pressure higher than 3000 atm, a substantial increase cannot be anticipated in the amount of formed crystals. Further, under such high pressures, the purity of the resultant polar vinyl compound is lowered to thereby cause the polymerizability improvement to be poor. Still further, an apparatus which can endure such high pressures is unfavorably large and expensive.

Generally, when the temperature of the crude polar vinyl compound is low, the crystallization pressure can be low, and contrarily when the temperature is high, a high pressure is required, in effectively carrying out the pressure crystallization operation of the crude polar vinyl compound.

In the present invention, the temperature of the crude polar vinyl compound is adjusted to 0°–100° C., preferably 10°–70° C. prior to feed into a pressure crystallizer (pressure cylinder). The temperature of the pressure cylinder of the pressure crystallizer is slightly increased by the adiabatic compression and the heat of crystallization when the crude polar vinyl compound is pressurized. The crystallization temperature for the polar vinyl compound is to be determined taking the above temperature increase into account. When the crystallization temperature is lower than 0° C., the concentration of the crude polar vinyl compound becomes too high to thereby lower its fluidity, so that feed of the crude polar vinyl compound into the pressure cylinder becomes difficult. On the other hand, when the crude polar vinyl compound is heated to a temperature higher than 100° C., thermal polymerization and alteration of the vinyl compound start to thereby invite quality and yield deteriorations.

Although the crude polar vinyl compound to be fed into the pressure cylinder in the present invention may be in the form of either liquid or a slurry containing seed crystals, the slurry is preferred for the following reason. That is, when the pressure cylinder of the pressure crystallizer is pressurized, not only is the pressure applied to the crude polar vinyl compound rapidly increased, but also the pressure energy is uniformly propagated through the liquid phase at sound speed. Accordingly, when the crude polar vinyl compound fed into the pressure cylinder contains no seed crystals, pressurization might bring the polar vinyl compound into the state of supersaturation, with the result that desirable growth of crystals cannot be attained. Therefore, it is desirable to allow the crude polar vinyl compound to stand still at a temperature and for a period of time which are satisfactory for formation of seed crystals to thereby form crystals of the polar vinyl compound prior to the pressure crystallization; or to partly split the flow of the crude polar vinyl compound to thereby cool the split part for formation of crystals, followed by mixing of the crude polar vinyl compound containing the seed crystals with the crude polar vinyl compound; or to add external seed crystals to the crude polar vinyl compound.

In the pressure crystallization, generally, the crystallization rate is greater than in the cooling crystallization, so that the time taken until reaching a nearly equilibrium state is shorter. However, it is preferred that the pressure be maintained until reaching a complete equilibrium for maximizing the amount of formed crystals per pressurization. Since the polar vinyl compound has relatively high crystallizability, the period in which the pressure is maintained is within 5 min, preferably 3 min.

In the present invention, a highly purified polar vinyl compound with high polymerizability can be obtained by separating the polar vinyl compound crystallized under pressure in the form of a solid phase (crystals) from the liquid phase in which impurities (e.g., substances inhibiting polymerization of the vinyl compound and raw materials used in the preparation of the polar vinyl compound) are concentrated. The pressure under which the solid phase is separated from the liquid phase is preferably in the range of 1000 to 2000 atm, which is slightly lower than the crystallization pressure. In this step, part of the crystals are dissolved in the remaining liquid phase (mother liquor) or sweat, so that the impurities contained in the crystals of the polar vinyl compound are discharged into the mother liquor, with the result that the obtained polar vinyl compound comes to have further improved polymerizability.

The crude polar vinyl compound to be treated in the present invention contains the polar vinyl compound having at least one member selected from among oxygen, nitrogen and sulfur atoms and impurities such as substances inhibiting polymerization of the vinyl compound.

The above polar vinyl compound includes, for example, compounds represented by the following general formulae (1), (2) and (3):

$$CH_2=CHNR^1COR^2 \qquad (1)$$

wherein each of $R^1$ and $R^2$ independently represents a hydrogen atom or a methyl group,

$$CH_2=CR^1COOR^2 \qquad (2)$$

wherein $R^1$ represents a hydrogen atom, a methyl group or a cyano group, and $R^2$ represents a hydrogen atom, an alkali metal, an alkyl group having 1 to 5 carbon atoms or a lower alkyl group, preferably a $C_2$–$C_4$ alkyl group, substituted with a hydroxyl, a dialkylamino or a quaternary ammonium group, and

$$CH_2=CR^1CONR^2R^3 \qquad (3)$$

wherein $R^1$ represents a hydrogen atom or a methyl group, and each of $R^2$ and $R^3$ independently represents a hydrogen atom, an alkyl group having 1 to 5 carbon atoms or a lower alkyl group, preferably a $C_2$–$C_4$ alkyl group, substituted with a hydroxyl, a dialkylamino, a sulfonic acid or a quaternary ammonium group.

Further, aromatic vinyl compounds each substituted with a hydroxyl group, an amino group, etc. can be used as the polar vinyl compound in the present invention.

Particular examples of the polar vinyl compounds include:

N-vinylcarboxamides such as N-vinylacetamide, N-vinyl-N-methylacetamide, N-vinylformamide and N-methyl-N-vinylformamide, acrylamides such as N-methylacrylamide, N-ethylacrylamide, N-isopropylacrylamide, monomethylolacrylamide, diacetonacrylamide, N,N-dimethylacrylamide, N,N-diethylacrylamide, N,N'-methylenebisacrylamide, 2-acrylamido-2-methylpropanesulfonic acid or sodium salt thereof and N-methylolacrylamide;

methacrylamide derivatives, acrylic acid, methacrylic acid, itaconic acid and acrylic or methacrylic esters such as pentaerythritol monoacrylate; and maleic anhydride, ethyl α-cyanoacrylate, o-, m- and p-hydroxystyrenes, o-, m- and p-aminostyrenes and N-vinylcarbazole. Of these polar vinyl compounds, N-vinylcarboxamides are preferred.

The impurities contained in the crude polar vinyl compound to be treated in the present invention include, for example, polymerization inhibiting substances and starting materials used in preparation of the polar vinyl compound. In particular, the polymerization inhibiting substances adversely affect the polymerization, or inhibits the polymerizability, of the polar vinyl compound (monomer). These polymerization inhibiting substances include polymerization inhibitors (substances) which completely block the polymerization of the polar vinyl compound for a certain period of time, polymerization retarders (substances) which retard the above polymerization and chain transfer agents (substances) which invite the lowering of the molecular weight, and are particularly not limited. Particular examples of the polymerization inhibiting substances include:

(1) metal salts capable of readily conducting monoelectron transfer reaction with propagating radicals, such as iron (III) salts and copper (II) salts;

(2) compounds capable of readily chain transfer reacting with primary radicals or propagating radicals to thereby form stable radicals, e.g., hydroquinone and other compounds each having a phenolic hydroxyl group, aromatic amines, allyl compounds and benzyl compounds; and (3) compounds capable of readily addition reacting with primary radicals or propagating radicals to thereby form stable radicals, such as oxygen, benzoquinone and nitroso compounds.

The above starting materials used in preparation of the polar vinyl compound are, for example, carboxamides, acetaldehyde, alcohols and N-(1-alkoxyethyl)-carboxamides.

The greater the polar vinyl compound content of he crude polar vinyl compound, the more preferably can the crude polar vinyl compound be used. It is preferred that the crude polar vinyl compound contain the polar vinyl compound in an amount of at least 40% by weight, especially at least 50% by weight, still especially at least 70% by weight. The crude polar vinyl compound may contain components other than the above impurities such as polymerization inhibiting substances, which are not particularly limited. When the polar vinyl compound content of the crude polar vinyl compound is lower than 40% by weight, the recovery of the polar vinyl compound is poor and often the polymerizability of the obtained polar vinyl compound is not satisfactory.

The above crude polar vinyl compound may be obtained by the process described in, for example, Japanese Patent Laid-open Publication Nos. 61(1986)-106546 (thermal decomposition process of ethylidenebisacetamide) and 50(1975)-76015 (preparation of secondary N-vinylcarboxamide). As long as the polar vinyl compound content is at least 40% by weight, the thermal decomposition products obtained by the above processes may either directly be used, or used after increasing the polar vinyl compound content by concentrating or distilling out the polar vinyl compound through distilling operation. The thus purified crude polar vinyl compound can preferably be employed because naturally the recovery as well as the purity and polymerizability of the polar vinyl compound are improved.

The N-vinylcarboxamide as the polar vinyl compound is unstable in water, and gradually decomposed by absorbing water contained in air. Especially, when an acid is present, it is extremely unstable and hydrolyzed. Therefore, when the N-vinylcarboxamide is used as the polar vinyl compound, it is preferred that the pressure crystallizer having the pressure separator, the raw material vessel and the auxiliary equipment such as the product container and the filtrate vessel be maintained in an atmosphere such as nitrogen and dry air, and that small amounts of a drying agent such as magnesium sulfate and a basic substance such as sodium bicarbonate be added to the crude polar vinyl compound in order to prevent the hydrolysis of the N-vinylcarboxamide.

Further, it is preferred that the pressure crystallization be performed in the presence of an alcohol (preferably an alcohol having up to 5 carbon atoms). The presence of an alcohol in carrying out the pressure crystallization lowers the melting point, and increases he solubility of the crude polar vinyl compound, so that the pressure crystallization can be performed at lower temperatures, thereby preventing the thermal deterioration of the polar vinyl compound.

In the first purification process for the polar vinyl compound according to the present invention, the liquid phase thus obtained as a by-product by the pressure crystallization of the crude polar vinyl compound often contains a significant amount of the vinyl compound per se as well as the polymerization inhibiting substances, starting materials used in synthesis of the polar vinyl compound and solvent. Therefore, the liquid phase may be recycled to a preceding step such as the step of reacting the vinyl compound, although it may directly be disposed of. Alternatively, the vinyl compound may be recovered from the liquid phase by pressure crystallization, cooling crystallization, distillation and other treatments. When the thus secondarily recovered compound does not exhibit satisfactory polymerizability, it may be mixed with the crude polar vinyl compound and recycled to the pressure crystallization step.

The second purification process for the polar vinyl compound according to the present invention will be described below. This second purification process for the polar vinyl compound comprises the steps of:

(1) crystallizing a polar vinyl compound from the crude polar vinyl compound according to the pressure crystallization process, and separating the crystals of the polar vinyl compound from a liquid phase to thereby obtain a highly purified polar vinyl compound;

(2) subjecting the liquid phase separated in the first step to the pressure crystallization process conducted at temperatures lower than in the first step, or to the cooling crystallization process, thereby obtaining second crystals of the polar vinyl compound; and (3) recycling the second crystals obtained in the second step into the crude polar vinyl compound for treatment in the first step.

First Step

The above first step comprises crystallizing a polar vinyl compound from the crude polar vinyl compound according to the pressure crystallization process, and separating the crystals of the polar vinyl compound from a liquid phase to thereby obtain a highly purified polar vinyl compound.

This first step is carried out in the same manner as in the above first purification process for the polar vinyl compound according to the present invention. That is, in the second purification process for the polar vinyl compound, the first purification process for the polar vinyl compound may first be performed and then followed by the above steps (2) and (3).

The liquid phase (mother liquor) obtained in the first step contains starting materials used in synthesis of the polar vinyl compound, such as carboxamides, N-(1-alkoxyethyl)carboxamides and ethylidenebiscarboxamides, and further contains optionally added alcohol, solvent and polymerization inhibiting substances (e.g., polymerization inhibitor). Therefore, the polar vinyl compound is recovered from the liquid phase (mother liquor) according to the pressure crystallization in the subsequent second step.

Second Step

In the second step, (a) crystals (second crystals) of the polar vinyl compound are obtained from the liquid phase (pressure crystallization waste fluid I) separated in the first step by the pressure crystallization process conducted at temperatures lower than in the first step, or alternatively (b) crystals (second crystals) of the polar vinyl compound are obtained from the liquid phase (pressure crystallization waste fluid I) separated in the first step by the cooling crystallization process.

(a) The procedure for obtaining crystals (second crystals) of the polar vinyl compound from the liquid phase (pressure crystallization waste fluid I) separated in the first step by the pressure crystallization process conducted at temperatures lower than in the first step, will be described below. In this second step, substantially the same pressure crystallization operations as in the first step (the first purification process) are carried out except for the crystallization temperature. That is, the concentration of the polar vinyl compound in the pressure crystallization waste fluid I to be treated in the second step is lower than that in the crude polar vinyl compound treated in the first step, so that the pressure crystallization is performed at temperatures lower than in the first step. It is preferred that the temperature of the pressure crystallization of the second step be more than 5°~20° C. lower than that of the first step depending on a kind of the polar vinyl compound used.

Illustratively, it is preferred in the second step that the temperature of the pressure crystallization waste fluid I be adjusted to −10° to 80° C., preferably 0° to 50° C. prior to feed into a pressure crystallizer (pressure cylinder).

The waste fluid (pressure crystallization waste fluid II) obtained by conducting the pressure crystallization of the pressure crystallization waste fluid I and separating the crystals (second crystals) of the polar vinyl compound in the second step contains a small amount of the polar vinyl compound, so that the polar vinyl compound may be recovered from the above waste fluid (liquid phase). However, since the concentration of the polar vinyl compound is low, the pressure crystallization must be performed at further lower temperatures, thereby bringing about a further decrease in separation efficiency. Therefore, the liquid phase resulting from the pressure crystallization of the second step (pressure crystallization waste fluid II) may be disposed of.

(b) Now, the cooling crystallization process will be described. When crystals (second crystals) of the polar vinyl compound are obtained from the liquid phase pressure crystallization waste fluid I) separated in the first step by the cooling crystallization process, the concentration of the polar vinyl compound in the pressure crystallization waste fluid I is so low that the pressure crystallization waste fluid I is preferably cooled to relatively low temperatures such as −10° to 80° C., especially 0° to 50° C. for crystallizing the polar vinyl compound.

The crystallizer suitable for use in the second step may be either continuous or batchwise. The formation of crystals may be effected by heat exchange with refrigerant or solvent evaporation for concentrating the liquid phase followed by cooling. There is no strict requirement with respect to the structure and mode for the pressure crystallization.

The crystals may be separated through a filter utilizing vacuum or pressure or through a filter utilizing gravity or centrifugal force. Although there is no particular limitation with respect to the filter, an automatic Nutsche filter such as Rosenmund filter is preferred, for example, when a high concentration slurry is filtered.

When the second step is conducted by this cooling crystallization process, although the liquid phase (pressure crystallization waste fluid I) separated from the crystals in the first step may directly be cooled to the above temperatures, use may be made of a recrystallization solvent being nonreactive with the polar vinyl compound and having appropriate dissolving ability. Examples of such recrystallization solvents include aromatic hydrocarbons such as benzene, toluene and xylene, aliphatic hydrocarbons such as hexane and cyclohexane, halogenated hydrocarbons such as chloroform, ethers such as diethyl ether and esters such as ethyl acetate.

Other conditions are the same as in the above pressure crystallization process (a) of the second step.

Third Step

In the third step, the second crystals obtained in the second step are recycled into the crude polar vinyl compound for treatment in the first step. When the amount of the second crystals recycled into the crude polar vinyl compound for treatment in the first step is small as compared with that of the crude polar vinyl compound and when the temperature thereof is not low, the second crystals are rapidly dissolved in the crude polar vinyl compound to thereby readily form a homogeneous solution. On the other hand, when the temperature of the second crystals is so low that it is difficult to dissolve them in the crude polar vinyl compound, the mixture of the crude polar vinyl compound to be treated in the first step and the second crystals may be heated to homogeneity. Alternatively, without dissolving, the second crystals may be fed in the form of a slurry to the first step for use as seed crystals. When the second crystals are used as seed crystals in the first step, it is preferred that the second crystals be pulverized prior to mixing into the crude polar vinyl compound for treatment in the first step.

The purification process of the present invention will be described in greater detail with respect to the N-vinylcarboxamide as an example of the polar vinyl compound, below.

First Process for Purifying N-Vinylcarboxamide

In the first process for purifying the N-vinylcarboxamide according to the present invention, the N-vinylcarboxamide (crude N-vinylcarboxamide) containing the N-vinylcarboxamide and impurities such as polymerization inhibiting substances and unreacted materials (e.g., carboxamides and N-(1-alkoxyethyl)carboxamides) is treated according to the pressure crystallization process, thereby separating the N-vinylcarboxamide from the impurities and consequently attaining purification of the N-vinylcarboxamide.

Examples of the N-vinylcarboxamides to be purified in the present invention include N-vinylacetamide, N-vinyl-N-methylacetamide, N-vinylformamide and N-methyl-N-vinylformamide. Of these, N-vinylacetamide is especially preferred.

It is preferred that the crude N-vinylcarboxamide to be employed in the present invention contain the N-vinylcarboamide in an amount of at least 40% by weight, especially at least 50% by weight, still especially at least 70% by weight. The crude N-vinylcarboxamide may contain other components, which are not particularly limited. Examples thereof include alcohols each having up to 5 carbon atoms, carboxamides, N-(1-alkoxyethyl)carboxamides and ethylidenebiscarboxamides. When the N-vinylcarboxamide content of the crude N-vinylcarboxamide is lower than 40% by weight, the recovery of the N-vinylcarboxamide is poor and the purity of the obtained N-vinylcarboxamide is so low that excellent polymerizability cannot be exhibited.

In the present invention, it is preferred that the pressure crystallization operation of the crude N-vinylcarboxamide be performed in the presence of an alcohol, preferably an alcohol having up to 5 carbon atoms. The presence of an alcohol in carrying out the pressure crystallization of the crude N-vinylcarboxamide lowers the melting point, and increases the solubility of the N-vinylcarboxamide, so that the pressure crystallization can be performed at lower temperatures, thereby preventing the thermal deterioration of the N-vinylcarboxamide.

Examples of such alcohols include methanol, ethanol, n- and isopropyl alcohols, n- and isobutyl alcohols, 2-butanol and n- and isoamyl alcohols and 2- and 3-pentanols. Of these, methanol is especially preferred. With respect to the N-vinylcarboxamide synthesized via N-(1-alkoxyethyl)carboxamide, it is preferred that the pressure crystallization be performed in the presence of the same type of alcohol as incidentally formed in the synthetic reaction, from the viewpoint that the pressure crystallization process can be simplified.

The crude N-vinylcarboxamide may be obtained by he process described in, for example, the above Japanese Patent Laid-open Publication Nos. 61(1986)-106546 and 50(1975)-76015. As mentioned above, it is preferred that the N-vinylcarboxamide content of the crude N-vinylcarboxamide be at least 50% by weight, from the viewpoint of improvements in the recovery, purity and polymerizability of the N-vinylcarboxamide.

The N-vinylcarboxamide is unstable in water, and gradually decomposed by absorbing water contained in air. Especially, when an acid is present, it is extremely unstable and hydrolyzed. Therefore, in the purification of the N-vinylcarboxamide, it is preferred that the pressure crystallizer having the pressure separator, the raw material vessel and the auxiliary equipment such as the product container and the filtrate vessel be maintained in an atmosphere such as nitrogen and dry air, and that a small amount of a drying agent such as magnesium sulfate be added to the crude N-vinylcarboxamide in order to prevent the hydrolysis of the N-vinylcarboxamide.

The N-vinylcarboxamide is extremely unstable in the presence of an acid, and if water is copresent, it is readily hydrolyzed. In the present invention, a basic compound is preferably added to the crude N-vinylcarboxamide prior to the pressure crystallization.

Examples of such basic compounds include:

sodium salts such as sodium carbonate, hydrogencarbonate, hydroxide, (hydrogen)phosphate and acetate;

potassium salts such as potassium carbonate, hydrogencarbonate, hydroxide, (hydrogen)phosphate and acetate; and aromatic amines such as N-phenyl-α-naphthylamine, 4,4'-bis(α,α-dimethylbenzyl)diphenylamine, N-phenyl-N'-(1,3-dimethylbutyl)-p-phenylenediamine, N-phenyl-N'-isopropyl-p-phenylenediamine, N-phenyl-N'-(1-methylheptyl)-p-phenylenediamine, N-phenyl-N'-cyclohexyl-p-phenylenediamine, N,N'-diphenyl-p-phenylenediamine, N,N'-di-β-naphthyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine and N-phenyl-N'-(p-toluenesulfonyl)-p-phenylenediamine. Of these, sodium salts are preferred, and sodium hydrogencarbonate is especially preferred.

The above basic compound is added to the crude N-vinylcarboxamide in a concentration of generally 10,000 to 1 ppm, preferably 1000 to 10 ppm. Even if the basic compound is added in a concentration of greater than 10,000 ppm, when it is an inorganic salt, it cannot be fully dissolved in the crude N-vinylcarboxamide and practically the effect corresponding to the added amount cannot be anticipated. On the other hand, when the basic compound is an aromatic amine, its complete removal would be difficult in the purification step, thereby rather lowering the polymerizability of the N-vinylcarboxamide. If the concentration of the basic compound is less than 1 ppm, there is substantially no effect as a stabilizer exhibited.

In the present invention, the crystallization pressure is generally in the range of 500 to 3000 atm and preferably in the range of 1000 to 2000 atm. When the crystallization pressure is lower than 500 atm, not only is the improvement in the polymerizability of the resultant N-vinylcarboxamide not substantial but also the amount of crystals obtained per crystallization operation is small to thereby cause the productivity to be low to economic disadvantage. On the other hand, even if the crystallization is performed under a pressure higher than 3000 atm, a substantial increase cannot be anticipated in the amount of formed crystals. Further, under such high pressures, the purity of the resultant N-vinylcarboxamide is lowered to thereby cause the polymerizability improvement to be poor. Still further, an apparatus which can endure such high pressures is unfavorably large and expensive.

Generally, when the temperature of the crude N-vinylcarboxamide is low, the crystallization pressure can be low, and contrarily when the temperature is high, a high pressure is required, in effectively carrying out the pressure crystallization operation of the crude N-vinylcarboxamide.

In the present invention, the temperature of the crude N-vinylcarboxamide is adjusted to 0°–100° C., preferably 10°–70° C. prior to feed into a pressure crystallizer (pressure cylinder). The temperature of the pressure cylinder of the pressure crystallizer is slightly increased by the adiabatic compression and the heat of crystallization when the crude N-vinylcarboxamide is pressurized. The crystallization temperature for the N-vinylcarboxamide is to be determined taking the above temperature increase into account. When the crystallization temperature is lower than 0° C., the concentration of the crude N-vinylcarboxamide becomes too high to thereby lower its fluidity, so that the feed of the crude N-vinylcarboxamide into the pressure cylinder becomes difficult. On the other hand, when the crude N-vinylcarboxamide is heated to a temperature higher than 100° C., thermal polymerization and alteration of the N-vinylcarboxamide start to hereby invite quality and yield deteriorations.

Although the crude N-vinylcarboxamide to be fed into the pressure cylinder in the present invention may be in the form of either liquid or a slurry containing seed crystals, the slurry is preferred for the following reason. That is, when the pressure cylinder of the pressure crystallizer is pressurized, not only is the pressure applied to the crude N-vinylcarboxamide rapidly increased, but also the pressure energy is uniformly propagated through the liquid phase at sound speed. Accordingly, when the crude N-vinylcarboxamide fed into the pressure cylinder contains no seed crystals, pressurization might bring the N-vinylcarboxamide into the state of supersaturation, with the result that desirable growth of crystals cannot be attained. Therefore, it is desirable to allow the crude N-vinylcarboxamide to stand still at a temperature and for a period of time which are satisfactory for formation of seed crystals to thereby form crystals of the N-vinylcarboxamide prior to the pressure crystallization; or to partly split the flow of the crude N-vinylcarboxamide to thereby cool the split part for formation of crystals, followed by mixing of the crude N-vinylcarboxamide containing the crystals with the crude N-vinylcarboxamide; or to add external seed crystals to the crude N-vinylcarboxamide.

In the pressure crystallization, generally, the crystallization rate is greater than in the cooling crystallization, so that the time taken until reaching a nearly equilibrium state is shorter. However, it is preferred that the pressure be maintained until reaching a complete equilibrium for maximizing the amount of formed crystals per pressurization. Since the N-vinylcarboxamide has relatively high crystallizability, the period in which the pressure is maintained is in the range of 0 to 10 min, preferably 0 to 5 min.

In the present invention, N-vinylcarboxamide with high polymerizability can be obtained by separating the N-vinylcarboxamide crystallized under pressure in the form of a solid phase (crystals) from the liquid phase in which polymerization inhibiting substances (impurities) are concentrated. The separation of the liquid phase from the solid phase is preferably performed while gradually reducing the pressure from the separation initiating pressure. At this stage, part of the crystals are dissolved in the remaining mother liquor or sweat, so that the impurities contained in the crystals of the N-vinylcarboxamide are discharged into the mother liquor, with the result that the obtained N-vinylcarboxamide comes to be highly purified and to have further improved polymerizability.

On the other hand, the liquid phase (mother liquor) contains starting materials used in synthesis of he N-vinylcarboxamide, such as carboxamides, N-(1-alkoxyethyl)carboxamides, alcohols and ethylidenebiscarboxamides. Accordingly, this liquid phase may be recycled to the steps for synthesizing and reacting starting materials of the N-vinylcarboxamide, e.g., the step of synthesizing the N-(1-alkoxyethyl)carboxamide or the step of synthesizing the ethylidenebiscarboxamide or the N-vinylcarboxamide. Also, the N-vinylcarboxamide may be recovered from the liquid phase through treatments, such as pressure crystallization, cooling crystallization and distillation.

Although the reason for the high purity and high polymerizability of the N-vinylcarboxamide obtained by the above purification has not been fully elucidated, it is believed that the following would bring about favorable effects. That is, the eutectic point under pressure, besides the sweating by pressure crystallization, is advantageous for the crystallization of the N-vinylcarboxamide as compared with the eutectic point observed in the cooling crystallization. Further, mechanical shock by agitation, etc. is less due to the pressure treatment in the pressure crystallization than in the cooling crystallization, so that not only are the conditions in the system more homogeneous but also the treatment time is shorter to thereby suppress the crystallization of impurities concentrated in the mother liquor. Still further, the separating operation is conducted at a relatively low temperature for a short time, so that the thermal deterioration of the N-vinylcarboxamide does not occur, and the obtained crystals are compacted into a cylindrical form to thereby have a small surface area, so that the deterioration by moisture absorption and oxidation is less likely.

The thus obtained N-vinylcarboxamide may be polymerized or copolymerized with another monomer to produce a water-soluble polymer, i.e., a homopolymer or copolymer of N-vinylcarboxamide.

The first process for purifying the N-vinylcarboxamide will now be described in greater detail, referring to FIG. 1.

FIG. 1 illustrates a flow chart of a synthesis of N-vinylacetamide comprising synthesis of dimethylacetal from acetaldehyde and methanol, purification thereof, reaction of dimethylacetal with acetamide to obtain N-vinylacetamide as a starting material of a hydrophilic polymer and separation thereof.

In FIG. 1, A is a reaction distillation column, B is a distillation column, C is a counter-current extraction column, D is a reactor for conversion to an ether amide, E is an acetal stripper, F is a methanol stripper, G is a reactor for decomposition of an ether amide, H is an N-vinylacetamide vacuum distillation column, I is a pressure crystallizer, and J is a pressure crystallizer or cooling crystallizer. The full lines and numerals 1 to 19 indicate the flow of materials.

Step of Acetal Synthesis:

An appropriate amount of acetaldehyde 1 as a starting material is fed into a lower part of the reaction distillation column A. A mixture of methanol 2 containing small amounts of acetal and water which is recovered at the counter-current extraction column C and methanol 3 recovered at the N-vinylacetamide vacuum distillation column H is continuously fed into the reaction distillation column A from an upper part thereof. An appropriate amount of an acid catalyst is dissolved in the methanol mixture. The water 5 originally contained in the starting acetaldehyde and formed during the reaction is discharged from the bottom of the column. The acid used as the acid catalyst is dissolved in this water, so that, according to necessity, appropriate neutralization and waste water treatment are conducted prior to the disposal thereof.

Step of Acetal Separation:

Reaction mixture 4 comprising methanol and dimethylacetal and methanol/dimethylacetal azeotrope 15 recovered by the demethanol distillation column (methanol stripper) F, together with light fluid 6 from the counter-current extraction column C which comprises n-hexane containing a small amount of dimethylacetal, are fed into the distillation column B, and distilled under atmospheric pressure, thereby obtaining highly purified acetal 8 from the bottom of the column. Methanol is distilled as a ternary azeotrope of hexane/methanol/dimethylacetal 7 from the top of the column. n-Hexane is fed in an amount needed to form the ternary azeotrope of hexane/methanol/dimethylacetal.

Step of Hexane Recovery:

The ternary azeotrope of hexane/methanol/dimethylacetal 7 withdrawn from the top of the distillation column B is counter-current contacted with a small amount of water in the counter-current extraction column C. Heavy fluid 2 which is an extraction residue obtained by extracting substantially the whole of methanol and most of dimethylacetal from the light fluid is withdrawn from the bottom of the column to thereby recover the same as part of the starting materials for the reaction distillation in the step of acetal synthesis. The light fluid 6 practically comprised of n-hexane is recovered from the top of the column and reutilized as an entrainer in the step of acetal separation. Step of α-Methoxyethylacetamide Synthesis:

α-Methoxyethylacetamide (hereinafter referred to as "MEA") is synthesized by the following conventional process (e.g., U.S. Pat. No. 4,554,377). That is, MEA is synthesized by the exchange reaction between dimethylacetal and acetamide as shown in the following formula:

$$(CH_3O)_2CHCH_3 + CH_3CONH_2 \longrightarrow \quad (I)$$

$$CH_3CH(OCH_3)NHCOCH_3 + CH_3OH$$
[MEA]

In this reaction, methanol is incidentally produced in an amount equimolar to that of MEA. The vapor pressures of acetamide and MEA are extremely close and also their solubilities in various solvents are similar, so that it is difficult to separate them by distillation or recrystallization. Therefore, the maximiation of the conversion of acetamide is desired. For sample, conversions of 95% or higher are desired. For keeping the conversion of acetamide high, it is preferred that the molar ratio of dimethylacetal to acetamide be about 20. When the molar ratio is lower than about 20, the conversion of acetamide may not be satisfactorily high. When the molar ratio is much greater than 20, the productivity is lowered and a significant acetamide conversion may not be attained. It is preferred that a small amount of methanol be added to the reaction system. This reaction is an equilibrium reaction, and the addition of methanol is not desirable from the viewpoint of the equilibrium relationship. However, the reaction of MEA with acetamide forms ethylidenebisacetamide (EBA) having extremely low solubility in dimethylacetal. If methanol is absent, the EBA is crystallized out of the system to thereby no longer participate in the equilibrium reaction, so that the equilibrium reaction is advanced rightward to thereby cause the yield of MEA to be poor. Therefore, it is preferred that methanol be added in a molar ratio of methanol to acetamide of about 3, for dissolving EBA incidentally formed in a small amount in accordance with the following formula II to thereby cause it to participate in the equilibrium reaction:

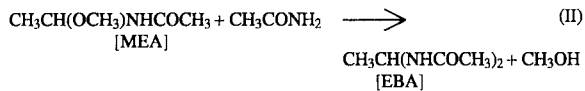

$$CH_3CH(OCH_3)NHCOCH_3 + CH_3CONH_2 \longrightarrow CH_3CH(NHCOCH_3)_2 + CH_3OH \quad (II)$$
[MEA] [EBA]

That is, it is preferred, for example, that the starting fluid for the reaction be composed of acetamide/dimethylacetal/methanol in molar proportions of 1/20/3.

The synthesis of MEA is carried out in the reactor for conversion to ether amide D which is packed with a strongly acidic ion exchange resin such as Amberlyst by feeding thereinto highly purified acetal 8 obtained from the bottom of the distillation column B, dimethylacetal 14 containing a small amount of methanol which is obtained from the bottom of the demethanol distillation column F and acetamide 10. A reaction mixture 11 comprising MEA, unreacted dimethylacetal, methanol formed by the reaction and a small amount of unreacted acetamide is obtained from the outlet of the reactor for conversion to ether amide D.

Step of Acetal Recovery:

The reaction mixture 11 obtained from the outlet of the reactor for conversion to ether amide D is fed into the acetal stripper E, where simple distillation is conducted to obtain dimethylacetal fraction 12 containing a small amount of methanol as light boiling fraction from the top of the column and also MEA fraction 13 as heavy boiling fraction from the bottom of the column.

Step of Methanol Recovery:

The dimethylacetal fraction 12 containing a small amount of methanol which is obtained from the top of the acetal stripper E is fed into the methanol stripper F. An azeotropic distillate of methanol and dimethylacetal 15 is obtained from the top of the column, and fed to the acetal purification step to obtain highly purified dimethylacetal. A dimethylacetal fraction 14 containing a less amount of methanol which is obtained from the bottom of the methanol stripper F is fed into the reactor for conversion to ether amide D, where it is reutilized as a starting material for the reaction of conversion to ether amide.

Step of N-Vinylacetamide Synthesis:

The MEA fraction 13 obtained from the bottom of the acetal stripper E is fed into the reactor for decomposition of ether amide G, where it is decomposed by thermal or acid-catalyst-using catalytic cracking into N-vinylacetamide and methanol. A methanol solution of N-vinylacetamide 16 is obtained from the outlet of the reactor for decomposition of ether amide G.

Step of N-Vinylacetamide Concentration:

The methanol solution of N-vinylacetamide 16 obtained from the outlet of the reactor for decomposition of ether amide G is fed into the N-vinylacetamide vacuum distillation column H, where vacuum distillation is conducted to effect separation of methanol 3 and crude N-vinylacetamide 17. The methanol 3 obtained from the top of the column is recycled to the reaction distillation column A for use in the step of acetal synthesis.

Step of N-Vinylacetamide Purification:

The crude N-vinylacetamide 17 obtained from the bottom of the vacuum distillation column H in the step of N-vinylacetamide concentration is purified by the pressure crystallizer I to thereby effect separation into highly purified N-vinylacetamide and waste fluid as mentioned above.

Below, the second process for purifying the N-vinylcarboxamide according to the present invention will be described in greater detail.

Second Process for Purifying N-Vinylcarboxamide

The second process for purifying the N-vinylcarboxamide according to the present invention comprises the steps of:

(1) crystallizing a N-vinylcarboxamide from a crude N-vinylcarboxamide according to the pressure crystallization process, and separating the crystals of the N-vinylcarboxamide from a liquid phase to thereby obtain a highly purified N-vinylcarboxamide;

(2) subjecting the liquid phase separated in the first step to the pressure crystallization process conducted at temperatures lower than in the first step, or the cooling crystallization process, thereby obtaining second crystals of the N-vinylcarboxamide; and (3) recycling the second crystals obtained in the second step into the crude N-vinylcarboxamide for treatment in the first step. The details of the above process is as described above.

The second process for purifying the N-vinylcarboxamide according to the present invention will now be described in greater detail, referring to FIG. 2.

Figure 2:
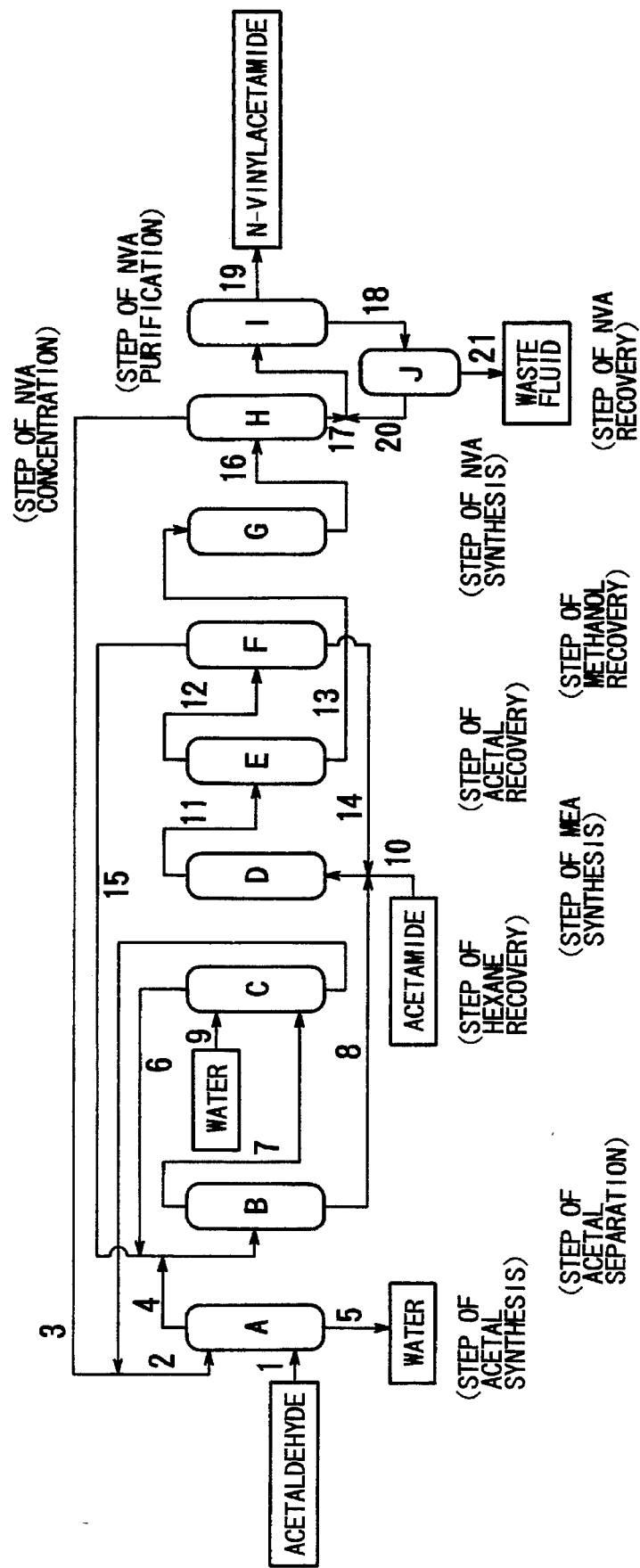

FIG. 2 illustrates a flow chart of a synthesis of N-vinylacetamide comprising synthesis of dimethylacetal from acetaldehyde and methanol, purification thereof, reaction of dimethylacetal with acetamide to obtain N-vinylacetamide as a starting material of a hydrophilic polymer and separation thereof.

In FIG. 2, A is a reaction distillation column, B is a distillation column, C is a counter-current extraction column, D is a reactor for conversion to an ether amide, E is an acetal stripper, F is a methanol stripper, G is a reactor for decomposition of an ether amide, H is an N-vinylacetamide vacuum distillation column, I is a pressure crystallizer, and J is a pressure crystallizer or cooling crystallizer. The full lines and numerals 1 to 19 indicate the flow of materials.

The above A to I have the same meanings as in FIG. 1.

In the second process for purifying the N-vinylcarboxamide according to the present invention, the same sequence of steps starting with the "step of acetal synthesis" and ending with the "step of N-vinylcarboxamide" as in the first process for purifying the N-vinylcarboxamide are carried out, followed by the first, second and third steps described below.

First Step (Step of N-Vinylacetamide Purification):

The crude N-vinylacetamide 17 obtained from the bottom of the vacuum distillation column H in the step of N-vinylacetamide concentration is purified by the pressure crystallizer I to thereby effect separation into highly purified N-vinylacetamide 19 and first step waste fluid 18.
Second Step (Step of N-Vinylacetamide Recovery):

The first step waste fluid 18 obtained in the step of N-vinylacetamide purification is treated by the pressure crystallizer J to thereby effect separation into crude N-vinylcarboxamide 20 and second step waste fluid 21.

The second step (step of N-vinylacetamide recovery) may be carried out according to the cooling crystallization process, as follows. That is, the first step waste fluid 18 obtained in the step of N-vinylacetamide purification is fed in the cooling crystallizer J (corresponding to the position J of FIG. 2) to thereby crystallize crude N-vinylcarboxamide 20, followed by separation by means of a solid liquid separator (not shown) into crude N-vinylacetamide 20 and second step waste fluid 21. Third Step (Step of Recycling Recovered N-Vinylcarboxamide)

The crude N-vinylcarboxamide 20 is combined with the crude N-vinylacetamide 17 obtained from the bottom of the vacuum distillation column H in the step of N-vinylacetamide concentration, and fed into the pressure crystallizer I for use in the first step (step of N-vinylacetamide purification), in which it is reutilized as crude N-vinylcarboxamide for obtaining highly purified N-vinylacetamide.

Although the reason for the high purity and high polymerizability of the N-vinylcarboxamide obtained by the N-vinylcarboxamide purification process of the present invention has not been fully elucidated, it is believed that the following would bring about favorable effects. That is, the eutectic point under pressure, besides the sweating by pressure crystallization, is advantageous for the crystallization of the N-vinylcaroxamide as compared with the eutectic point observed in the cooling crystallization. Further, the separating operation is conducted at a relatively low temperature for a short time, so that the thermal deterioration of the N-vinylcarboxamide does not occur, and the obtained crystals are compacted into a cylindrical form to thereby have a small surface area, so that the deterioration by moisture absorption is less likely.

The thus obtained N-vinylcarboxamide may be polymerized or copolymerized with another monomer to thereby produce a water-soluble polymer, i.e., a homopolymer or copolymer of N-vinylcarboxamide.

EXAMPLES

The present invention will further be illustrated with reference to the following Examples and Comparative Examples, which should not be construed as limiting the scope of the invention.

Example 1

Catalytic hydration of acrylonitrile was carried out with the use of a catalyst containing copper, thereby obtaining a reaction mixture containing acrylamide. Unreacted acrylonitrile was distilled off from the reaction mixture according to the customary procedure, thereby obtaining a 50% by weight aqueous acrylamide solution.

The above aqueous acrylamide solution (I) was cooled to 10° C., put in a pressure crystallizer, and pressurized at 10° C. under 1800 kg/cm$^2$ until acrylamide was crystallized. The crystals were separated from the liquid phase (mother liquor). Thus, acrylamide having a purity of 99.9% was obtained.

The polymerizability of the obtained acrylamide was evaluated as follows. Water was added to obtain a 20% by weight solution, and 600 ppm of V-50 (N,N'-azobis(2-amidinopropane))dihydrochloride was added to the solution. The mixture was heated in a bath thermostatically controlled at 45° C. for 10 min. Thereafter, the mixture was diluted with water to 10% by weight, and the viscosity thereof was measured by the use of BL viscometer (rotating speed: 30 rpm) at 30° C. The viscosity was 120 cps.

Comparative Example 1

The 50% by weight aqueous acrylamide solution (I) obtained in Example 1 was cooled to 5° C., and crystallized acrylamide was separated by filtration and dried at reduced pressure at 40° C. for 6 hr. The resultant acrylamide contained 10 ppm of copper ions and 0.5% of polymer. The polymerizability evaluation conducted in the same manner as in Example 1 showed that the viscosity was 5 cps.

Comparative Example 2

Copper was removed from the 50% by weight aqueous acrylamide solution (I) obtained in Example 1 by the use of a strongly acidic cation exchange resin, and neutralized, thereby obtaining a 50% by weight aqueous acrylamide solution. The polymerizability evaluation conducted in the same manner as in Example 1 showed that the viscosity was 85 cps.

Example 2

640 g (4.5 mol) of a 50% by weight aqueous acrylamide solution and 11.7 ml of a 0.1N aqueous sodium hydroxide solution were put in a four-necked flask equipped with an agitator, a cooler and a thermometer, and the temperature thereof was adjusted to 30° C. A 37% by weight formaldehyde solution in which formic acid had been neutralized with sodium hydroxide (3.8 mol) was added while agitating. Four hours later, the formation of N-methylolacrylamide was 75%. The reaction mixture was neutralized with 0.1N sodium dihydrogenphosphate.

The neutralized reaction mixture (II) was cooled to 20° C., put in a pressure crystallizer, and pressurized at 20° C. under 1800 kg/cm$^2$ until N-methylolacrylamide was crystallized. The crystals were separated from the liquid phase (mother liquor). Thus, N-methylolacrylamide having a purity of 99.9% was obtained.

The polymerizability of the obtained N-methylolacrylamide was evaluated as follows. Water was added to obtain a 20% by weight solution, and 600 ppm of V-50 (N,N'-azobis(2-amidinopropane))dihydrochloride was added to the solution. The mixture was heated in a bath thermostatically controlled at 45° C. for 10 min. Thereafter, the mixture was diluted with water to 10% by weight, and the viscosity thereof was measured by he use of BL viscometer (rotating speed: 30 rpm) at 30° C. The viscosity was 150 cps.

Comparative Example 3

For evaluating the polymerizability of the neutralized reaction mixture (II) obtained in Example 2, water was added to the neutralized reaction mixture (II) until the concentration became 20% by weight, and the viscosity was measured in the same manner as in Example 2. The viscosity was 10 cps.

Example 3

5.9 g (0.1 mol) of acetamide, 40 g (0.67 mol) of isopropyl alcohol, 2.16 g (15 mmol) of ethylidenebisacetamide and 14.6 g (0.1 mol) of acetaldehyde diisopropyl acetal were fed into a three-necked flask (200 ml) equipped with a thermometer and a dry ice/ethanol trap, and agitated at 45° to 48° C. until a homogeneous solution was obtained. A liquid obtained by dissolving 0.43 g of concentrated sulfuric acid (0.1% by weight of the charge) in 2 g (33 mmol) of isopropyl alcohol (same in the following Examples) was added to the solution, and agitated. Subsequently, 1.76 g (0.4 mol) of acetaldehyde was added over a period of 3 min by means of a dropping funnel. After the completion of the addition, the mixture was heated at 50° C. for 3 hr. The catalyst was neutralized, and measurements were made by gas chromatography. The conversion of acetamide was 88%, the selectivity for N-(α-propoxyethyl)acetamide was 94%, and the selectivity for ethylidenebisacetamide as a by-product was 5.3%. With respect to the increase or decrease of the formation of the acetal, within the range of 30 min to 3 hr in reaction time, there was a decrease of 1 mmol of the addition amount, while ethylidenebisacetamide reached an equilibrium.

N-(α-propoxyethyl)acetamide was obtained from the resultant reaction mixture by vacuum distillation, and it was thermally decomposed into N-vinylacetamide and isopropyl alcohol under conditions such that the temperature was 450° C. and that the residence time was 1 sec.

The thus obtained thermally decomposed reaction mixture (III) was cooled to 20° C., put in a pressure crystallizer, and pressurized at 20° C. under 1800 kg/cm$^2$ until N-vinylacetamide was crystallized. The crystals were separated from the liquid phase (mother liquor). Thus, N-vinylacetamide having a purity of 99.9% was obtained. The polymerizability of the obtained N-vinylacetamide was evaluated as follows. Water was added to obtain a 20% by weight solution, and 600 ppm of V-50 (N,N'-azobis(2-amidinopropane))dihydrochloride was added to the solution. The mixture was heated in a bath thermostatically controlled at 45° C. for 10 min. Thereafter, the mixture was diluted with water to 10% by weight, and the viscosity thereof was measured by the use of BL viscometer (rotating speed: 30 rpm) at 30° C. The viscosity of the solution was 130 cps.

Comparative Example 4

The thermally decomposed reaction mixture (III) obtained in Example 3 was vacuum distilled by means of 20-plate Oldershaw rectifying column at a reflux ratio of 2 and at a pressure of 3 torr, thereby obtaining N-inylacetamide having a purity of 97.5%. The evaluation of the polymerizability of the N-vinylacetamide conducted in the same manner as in Example 3 showed that the viscosity of the solution was 40 cps.

Example 4

Mixture (IV) comprised of 87% by weight of N-vinylacetamide, 9% by weight of N-(α-methoxyethyl)acetamide and 4% by weight of acetamide was cooled to 20° C., fed into a pressure crystallizer, and pressurized at 50° C. under 1800 kg/cm$^2$ until N-vinylacetamide was crystallized. The crystals were separated from the liquid phase (mother liquor). Thus, N-vinylacetamide having a purity of 99.9% which contained 600 ppm of N-(α-methoxyethyl)acetamide and 300 ppm of acetamide was obtained at a recovery of 50%.

The polymerizability of the obtained N-vinylacetamide was evaluated as follows. Water was added to obtain a 20% by weight solution, and 600 ppm of V-50 (N,N'-azobis(2-amidinopropane))dihydrochloride was added to the solution. The mixture was heated in a bath thermostatically controlled at 45° C. for 10 min. Thereafter, the mixture was diluted with water to 10% by weight, and the viscosity thereof was measured by the use of BL viscometer (rotating speed: 30 rpm) at 30° C. The viscosity of the solution was 150 cps.

Comparative Example 5

The mixture (IV) mainly comprised of N-vinylacetamide which was employed in Example 4 was fed into a rectifying column having 20 plates in terms of theoretical plate number, packed with 5 mm Sluzer packings, at the 10th (counted from the top) column and into a heating oven connected to the bottom of the column to thereby carry out rectification at a reflux ratio of 3 and at a vacuum of 2 mmHg. N-vinylacetamide having a purity of 89% which contained 7% by weight of N-(-methoxyethyl)acetamide and 4% by weight of acetamide was withdrawn from the top of the column.

The evaluation of the polymerizability of the obtained fraction conducted in the same manner as in Example 4 showed that the viscosity of the solution was 50 cps.

Example 5

Vapor phase oxidation of propylene was conducted to prepare acrylic acid, which was subjected to absorption in water, extraction from the aqueous solution with butyl acetate, azeotropic distillation and rectification. Thus, crude acetic acid (V) was obtained, which contained 500 ppb of acrolein, 2000 ppm of acetic acid, 1500 ppb of benzaldehyde, 700 ppb of furfurylaldehyde, 400 ppm of propionic acid and 2000 ppm of acrylic acid dimer.

The obtained crude acrylic acid was cooled to 15° C., fed into a pressure crystallizer, and pressurized at 18° C. under 1800 kg/cm$^2$ until acrylic acid was crystallized. The crystals were separated from the liquid phase (mother liquor). Thus, acrylic acid having a purity of 99.9% was obtained at a recovery of 75%. The acrylic acid contained 10 ppb of acrolein, 25 ppm of acetic acid, 110 ppb of benzaldehyde, 5 ppb of furfurylaldehyde, 30 ppm of propionic acid and 15 ppm of acrylic acid dimer.

The polymerizability of the obtained acrylic acid was evaluated as follows. In a test tube, water was added to obtain a 20% by weight solution, and 2% by weight of V-50 (N,N'-azobis(2-amidinopropane))dihydrochloride was added to the solution. The mixture was heated in a bath thermostatically controlled at 45° C. 10 min later, the temperature of the aqueous acrylic acid solution increased to 46.5° C.

Comparative Example 6

The crude acetic acid (V) obtained in Example 5 was vacuum distilled at 60° C. and at 4 mmHg. The distilled acrylic acid contained 300 ppb of acrolein, 600 ppm of cetic acid, 400 ppb of benzaldehyde, 500 ppb of furfurylaldehyde, 300 ppm of propionic acid and 150 ppm of acrylic acid dimer. The polymerizability of the acrylic acid thus rectified by distillation was evaluated in the same manner as in Example 5. Even when heated in a bath thermostatically controlled at 45° C. for 15 min, the temperature of the aqueous acrylic acid solution did not increase to 46° C.

Example 6

[Step of Acetal Synthesis]

Methanol containing 0.5% by weight of sulfuric acid was fed into 25-plate glass-made Oldershaw rectifying column at the 5th (counted from the top) plate at a rate of 180 g/hr, and also acetaldehyde at the 15th (counted from the top) plate at a rate of 72 g/hr. A lower part of the rectifying column was provided with a 500 ml flask containing 100 g of water, which was heated at 100° C. The flask contents were withdrawn at a rate of 29 g/hr. The withdrawn fluid contained substantially no organic materials. A mixture of dimethylacetal and methanol was withdrawn from the top of the column at a reflux ratio of 2 and at a rate of 221 g/hr. The withdrawn distillate contained substantially none of water and acetaldehyde. The acetaldehyde conversion was 100% and the dimethylacetal yield was 100%.

[Step of Acetal Separation]

n-Hexane was fed into 25-plate glass-made Oldershaw rectifying column at the 1st (counted from the top) plate at a rate of 56 g/hr, and also dimethylacetal containing 28% by weight of methanol at the 10th (counted from the top) plate at a rate of 71 g/hr. Heating was performed to keep the reflux ratio of 2 and the temperature of the top of the column at 50° C., respectively. A lower part of the rectifying column was provided with a 500 ml flask containing 100 g of dimehylacetal, which was heated in an oil bath of 110° C. The flask contents were withdrawn at a rate of 47 g/hr. The withdrawn fluid was dimethylacetal containing 0.3% of methanol and containing substantially no n-hexane. A mixture of dimethylacetal, methanol and n-hexane was withdrawn from the top of the column at a rate of 80 g/hr. The withdrawn distillate and bottoms liquid both contained substantially none of water and acetaldehyde.

[Step of Hexane Separation and Recovery]

A light fluid of the distillate obtained in the step of acetal separation was fed into a vertically movable liquid-liquid counter-current extraction column of 50 mm in inner diameter of column having 30 baffle plates disposed at 25 mm intervals through a lower part thereof at a rate of 2370 g/hr, while water as a heavy fluid was fed thereinto through an upper part thereof at a rate of 13 g/hr, thereby effecting counter-current extraction. The baffle plates had vertical reciprocating motions of 12.5 mm stroke and 150 cycle. The extracted light fluid contained substantially none of water and methanol, which was n-hexane containing 3% by weight of dimethylacetal. The heavy fluid contained 80% by weight of methanol, 5% by weight of dimethylacetal, 1% by weight of n-hexane and the balance of water.

[Step of α-Methoxyethylacetamide Synthesis]

Highly purified dimethylacetal obtained in the step of acetal separation was mixed with the dimethylacetal containing methanol obtained in the step of methanol recovery, and dry acetamide was dissolved in the mixture. Thus, a 1:20:3 starting fluid of acetamide, dimethylacetal and methanol was obtained. This fluid was fed into a reaction tube of 40 mm in inner diameter packed with 60 ml of strongly acidic ion exchange resin Amberlyst 15 at a lower part thereof at a rate of 5 ml/hr. The reaction tube was provided with a jacket through which hot water of 55° C. was allowed to flow to thereby control the reaction temperature at 55° C. A quantitative analysis of the reaction mixture obtained through the outlet at an upper part of the reactor showed that the reaction mixture was composed of acetamide, dimethylacetal, methanol and MEA in approximate molar proportions of 0:19:4:0.9, that the acetamide conversion was 98%, and the yield of α-methoxyethylacetamide (MEA) was 90%.

[Step of Acetal Recovery]

The reaction mixture obtained in the step of α-methoxyethylacetamide synthesis was fed into a continuous thin-film flash evaporator provided with a jacket having a heating surface area of 0.04 m² whose pressure was reduced to 100 mmHg, at a rate of 600 g/hr. Heating medium of 90° C. was circulated through the jacket. Evaporation residue practically composed of α-methoxyethylacetamide was obtained at a rate of 17 g/hr. Liquid condensate of volatile composed of dimethylacetal containing 7% by weight of methanol was obtained at a rate of 583 g/hr.

[Step of Methanol Recovery]

The dimethylacetal fraction containing 7% by weight of methanol obtained in the step of acetal recovery was fed into 25-plate glass-made Oldershaw rectifying column at the 10th (counted from the top) plate at a rate of 200 g/hr. Heating was performed to keep the reflux ratio at 6 and the temperature of the top of the column at 58° C., respectively. A lower part of the rectifying column was provided with a 500 ml flask, which was heated in an oil bath of 110° C. The flask contents were withdrawn at a rate of 185 g/hr. The withdrawn fluid was dimethylacetal containing 5.6% of methanol. An azeotropic mixture of dimethylacetal and methanol (24% by weight of methanol) was withdrawn from the top of the column at a rate of 15 g/hr.

[Step of N-Vinylacetamide Synthesis]

The fluid practically composed of α-methoxyethylacetamide which was obtained in the step of acetal recovery was fed into a stainless steel reactor of 20 mm in inner diameter and 2 m in full length heated to 450° C., whose pressure was reduced to 40 mmHg, at a rate of 20 ml/min. A mixture of N-vinylacetamide and methanol formed by thermal decomposition was condensed by means of a condenser attached to the outlet of the reactor to thereby recover the same. The α-methoxyethylacetamide conversion was 95%.

[Step of N-Vinylacetamide Concentration]

The reaction mixture obtained in the step of N-vinylacetamide synthesis was fed into 10-plate glass-made Oldershaw rectifying column at the 10th (counted from the top) plate at a rate of 200 g/hr. The pressure was reduced to 200 mmHg, and heating was performed to keep the reflux ratio at 2 and the temperature of the top of the column at 40° C., respectively. A lower part of the rectifying column was provided with a 500 ml flask, which was heated in an oil bath of 110° C. The flask contents were withdrawn at a rate of 155 g/hr. The withdrawn fluid was crude N-vinylacetamide containing 94% of N-vinylacetamide. Methanol was withdrawn from the top of the column at a rate of 45 g/hr.

[Step of N-Vinylacetamide Purification]

The temperature of the crude N-vinylacetamide solution obtained in the step of N-vinylacetamide concentration was adjusted to 50° C., and this crude N-vinylacetamide solution was subjected to pressure crystallization in a high pressure vessel at 50° C. under 1800 kg/cm². Thus, N-vinylacetamide was crystallized, and the crystals were separated from the mother liquor. As a result, N-vinylacetamide having a purity of 99.9% was obtained. The polymerizability of the obtained N-vinylacetamide was evaluated as follows. Water was added to obtain a 20% by weight solution, and 600 ppm of V-50 (N,N'-azobis(2-amidinopropane))dihydrochloride was added to the solution. The mixture was heated in a bath thermostatically controlled at 45° C. for 10 min. Thereafter, the mixture was diluted with water to 10% by weight, and the viscosity thereof was measured by the use of BL viscometer (rotating speed: 30 rpm) at 30° C. The viscosity of the solution was 150 cps.

Comparative Example 7

The reaction mixture obtained in the step of N-vinylacetamide synthesis of Example 6 was fed into 10-plate glass-made Oldershaw rectifying column at the 10th (counted from the top) plate at a rate of 200 g/hr. The pressure was reduced to 200 mmHg, and heating was performed to keep the reflux ratio at 2 and the temperature of the top of the column at 40° C., respectively. A lower part of the rectifying column was provided with a 500 ml flask, which was heated in an oil bath of 80° C. The flask contents were withdrawn at a rate of 155 g/hr. The withdrawn fluid was a methanol solution containing 94% of N-vinylacetamide. Methanol was withdrawn from the top of the column at a rate of 45 g/hr.

The above fluid withdrawn from the flask (methanol solution containing 94% of N-vinylacetamide) was fed into a rectifying column having 20 plates in terms of theoretical plate number, packed with 5 mm Sluzer packings, at the 10th (counted from the top) plate at a rate of 155 g/hr. The pressure was reduced to 2 mmHg, and the reflux ratio was set at 3. A lower part of the rectifying column was provided with a 500 ml flask, which was heated in an oil bath of 105° C. The flask contents were withdrawn at a rate of 140 g/hr. The withdrawn fluid was N-vinylacetamide. Methanol containing a small amount of acetamide was withdrawn from the top of the column at a rate of 15 g/hr. The polymerizability of the obtained N-vinylacetamide was evaluated in the same manner as in Example 1. The viscosity of the solution was 50 cps.

Example 7

The same sequence of steps starting with the step of acetal synthesis and ending with the step of N-vinylacetamide concentration as in Example 6 were carried out, followed by the following steps.

[First Step]

The temperature of 21.3 g of the concentrated fluid obtained in the step of N-vinylacetamide synthesis was adjusted to 50° C., and the fluid was pressurized to 1800 kg/cm$^2$ in a high pressure vessel for 5 min. Thus, N-vinylacetamide was crystallized, and the crystals were separated at 50° C. from the liquid phase (mother liquor). As a result, 8.1 g of N-vinylacetamide having a purity of 99.6% was obtained, together with 13.1 g of waste fluid. The recovery of N-vinylacetamide was 47%, and the waste fluid was composed of 74% of N-vinylacetamide, 16% of α-methoxyethylacetamide and 10% of acetamide. The polymerizability of the obtained N-vinylacetamide was evaluated as follows. Water was added to obtain a 20% by weight solution, and 600 ppm of V-50 (N,N'-azobis(2-amidinopropane))dihydrochloride was added to the solution. The mixture was heated in a bath thermostatically controlled at 45° C. for 10 min. Thereafter, the mixture was diluted with water to 10% by weight, and the viscosity thereof was measured by the use of BL viscometer (rotating speed: 30 rpm) at 30° C. The viscosity of the solution was 150 cps.

[Second Step]

The temperature of 21.3 g of the waste fluid obtained in the above first step was adjusted to 25° C., and the fluid was pressurized to 1800 kg/cm$^2$ in a high pressure vessel and pressurized for 5 min. Thus, N-vinylacetamide was crystallized, and the crystals (second crystals) were separated at 25° C. from the liquid phase (mother liquor). As a result, 5.7 g of N-vinylacetamide having a purity of 99.4% was obtained, together with 15.6 g of waste fluid. The recovery of N-vinylacetamide was 36%, and the waste fluid was composed of 59% of N-vinylacetamide, 22% of α-methoxyethylacetamide and 13% of acetamide. The polymerizability of the obtained N-vinylacetamide was evaluated in the same manner as above. The viscosity of the solution was 63 cps.

[First Step in which Second Crystals were Recycled]

14.8 g of the concentrate obtained in the step of N-vinylacetamide synthesis and 6.4 g of the second crystals obtained in the second step were mixed together to thereby dissolve the second crystals in the concentrate. The temperature of the resultant fluid was adjusted to 50° C., and the fluid was pressurized to 1800 kg/cm$^2$ in a high pressure vessel and pressurized for 5 min. Thus, N-vinylacetamide was crystallized, and the crystals were separated at 50° C. from the mother liquor. As a result, 10.3 g of N-vinylacetamide having a purity of 99.8% was obtained, together with 10.5 g of waste fluid. The recovery of N-vinylacetamide was 56%, and the waste fluid was composed of 74% of N-vinylacetamide, 15% of α-methoxyethylacetamide and 8% of acetamide. The polymerizability of the obtained N-vinylacetamide was evaluated in the same manner as above. The viscosity of the solution was 133 cps.

The above second step followed by the above first step in which the second crystals were recycled, was repeated three times. Then, the amount of obtained crystals and the composition of the waste fluid reached substantially the steady state, at which the N-vinylacetamide recovery on the basis of the N-vinylacetamide of the concentrate obtained in the step of N-vinylacetamide step was 70%.

Comparative Example 8

The reaction mixture obtained in the step of N-vinylacetamide synthesis of Example 7 was fed into 10-plate glass-made Oldershaw rectifying column at the 10th (counted from the top) plate at a rate of 200 g/hr. The pressure was reduced to 200 mmHg, and heating was performed to keep the reflux ratio at 2 and the temperature of the top of the column at 40° C., respectively. A lower part of the rectifying column was provided with a 500 ml flask, which was heated in an oil bath of 80° C. The flask contents were withdrawn at a rate of 155 g/hr. The withdrawn fluid was a methanol solution containing 94% of N-vinylacetamide. Methanol was withdrawn from the top of the column at a rate of 45 g/hr. The above fluid withdrawn from the flask (methanol solution containing 94% of N-vinylacetamide) was fed into a rectifying column having 20 plates in terms of theoretical plate number, packed with 5 mm Sluzer packings, at the 10th (counted from the top) plate at a rate of 155 g/hr. The pressure was reduced to 2 mmHg, and the reflux ratio was set at 3. A lower part of the rectifying column was provided with a 500 ml flask, which was heated in an oil bath of 105° C. The flask contents were withdrawn at a rate of 140 g/hr. The withdrawn fluid was N-vinylacetamide. Methanol containing a small amount of acetamide was withdrawn from the top of the column at a rate of 15 g/hr. The polymerizability of the obtained N-vinylacetamide was evaluated in the same manner as in Example 1. The viscosity of the solution was 5 cps.

Example 8

The procedure of Example 7 was repeated in the same manner as described therein, except that the second step was carried out as follows.

[Second Step]

21.0 g of the waste fluid obtained in the first step of Example 7 was cooled to 10° C., and filtered through a 200-mesh stainless steel net. The resultant cake was pressurized at 100 kg/cm², and the pressure was maintained for 5 min to thereby squeeze the mother liquor. Thus, 4.8 g of N-vinylacetamide having a purity of 99.4% was obtained, together with 16.2 g of waste fluid. The recovery of N-vinylacetamide was 31%, and the waste fluid was composed of 66% of N-vinylacetamide, 21% of α-methoxyethylacetamide and 13% of acetamide. The polymerizability of the obtained N- vinylacetamide was evaluated in the same manner as above. The viscosity of the solution was 43 cps.

[First Step in which Second Crystals were Recycled]

14.8 g of the concentrate obtained in the step of N-vinylacetamide synthesis and 6.4 g of the crystals obtained in the second step were mixed together to thereby dissolve the crystals in the concentrate. The temperature of the resultant fluid was adjusted to 50° C., and the fluid was pressurized to 1800 kg/cm² in a high pressure vessel for 5 min. Thus, N-vinylacetamide was crystallized, and the crystals were separated at 50° C. from the mother liquor. As a result, 10.2 g of N-vinylacetamide having a purity of 99.7% was obtained, together with 10.5 g of waste fluid. The recovery of N-vinylacetamide was 55%, and the waste fluid was composed of 70% of N-vinylacetamide, 15% of α-methoxyethylacetamide and 8% of acetamide. The polymerizability of the obtained N-vinylacetamide was evaluated in the same manner as above. The viscosity of the solution was 121 cps.

The above second step followed by the above first step in which the second crystals were recycled, was repeated three times. Then, the amount of obtained crystals and the composition of the waste fluid reached substantially the steady state, at which the N-vinylacetamide recovery on the basis of the N-vinylacetamide of the concentrate obtained in the step of N-vinylacetamide step was 68%.

EFFECT OF THE INVENTION

The present invention ensures ready and efficient production of a polar vinyl compound such as N-vinylcarboxamide which is highly purified and thus has high polymerizability from a crude polar vinyl compound containing impurities such as polymerization inhibiting substances and starting materials used in synthesis of the polar vinyl compound.

We claim:

1. A process for purifying a polar vinyl compound, comprising pressurizing crude polar vinyl compound containing impurities, including polymerization inhibiting substances and starting materials used in preparation of the polar vinyl compound, to 500~3000 atm at 0°~100° C., the polar vinyl compound having at least one member selected from the group consisting of an oxygen atom, a nitrogen atom and a sulfur atom, to thereby form crystals of the polar vinyl compound and separating the crystals of the polar vinyl compound from a liquid phase under pressure to thereby obtain a highly purified polar vinyl compound.

2. The process as claimed in claim 1, wherein the polar vinyl compound is an N-vinylcarboxamide.

3. The process as claimed in claim 1, wherein the polar vinyl compound is a compound represented by the general formula:

$$CH_2=CHNR^1COR^2 \qquad (1)$$

wherein each of $R^1$ and $R^2$ independently represents a hydrogen atom or a methyl group.

4. The process as claimed in claim 1, wherein the polar vinyl compound is a compound represented by the general formula:

$$CH_2=CR^1COOR^2 \qquad (2)$$

wherein $R^1$ represents a hydrogen atom, a methyl group or a cyano group, and $R^2$ represents a hydrogen atom, an alkali metal atom, an alkyl group having 1 to 5 carbon atoms or a lower alkyl group substituted with a hydroxyl group, a dialkylamino group or a quaternary ammonium group.

5. The process as claimed in claim 1, wherein the polar vinyl compound is a compound represented by the general formula:

$$CH_2=CR^1CONR^2R^3 \qquad (3)$$

wherein $R^1$ represents a hydrogen atom or a methyl group, and each of $R^2$ and $R^3$ independently represents a hydrogen atom, an alkyl group having 1 to 5 carbon atoms or a lower alkyl group substituted with a hydroxyl group, a dialkylamino group, a sulfonic acid group or a quaternary ammonium group.

6. The process as claimed in claim 1, wherein the crude polar vinyl compound contains an N-vinylcarboxamide in an amount of at least 40% by weight.

7. The process as claimed in claim 2, wherein crystallization from the crude polar vinyl compound is performed in the presence of an alcohol.

8. The process as claimed in claim 2, wherein crystallization from the crude polar vinyl compound is performed in the presence of a basic compound.

9. A process for purifying a polar vinyl compound, as claimed in claim 1 including separating a polar vinyl compound from crude polar vinyl compound and purifying the same to obtain a highly purified polar vinyl compound, which comprises the steps of:

(1) crystallizing a polar vinyl compound from a crude polar vinyl compound according to a pressure crystallization process, and separating the crystals of the polar vinyl compound from a liquid phase to thereby obtain a highly purified polar vinyl compound;

(2) subjecting the liquid phase separated in the first step to the pressure crystallization process conducted at temperatures lower than in the first step, thereby obtaining second crystals of the polar vinyl compound; and (3) recycling the second crystals obtained in the second step into the crude polar vinyl compound for treatment in the first step.

10. A process for purifying a polar vinyl compound, as claimed in claim 1 including separating a polar vinyl compound from crude polar vinyl compound and purifying the same to obtain a highly purified polar vinyl compound, which comprises the steps of:

(1) crystallizing a polar vinyl compound from crude polar vinyl compound according to the pressure crystallization process, and separating the crystals of the polar vinyl compound from a liquid phase to thereby obtain a highly purified polar vinyl compound;

(2) subjecting the liquid phase separated in the first step to the cooling crystallization process, thereby obtaining second crystals of the polar vinyl compound; and (3) recycling the second crystals obtained in the second step into the crude polar vinyl compound for treatment in the first step.

11. The process as claimed in claim 9, wherein the polar vinyl compound is an N-vinylcarboxamide.

12. The process as claimed in claim 10, wherein the polar vinyl compound is an N-vinylcarboxamide.

* * * * *